United States Patent [19]

Sone et al.

[11] Patent Number: 5,948,403

[45] Date of Patent: Sep. 7, 1999

[54] CORNEAL ANGIOGENESIS INHIBITOR

[75] Inventors: Saburo Sone; Akemi Kajita; Yu-ichiro Satoh, all of Kanagawa, Japan

[73] Assignee: Toray Industries, Inc., Tokyo, Japan

[21] Appl. No.: 08/737,272

[22] PCT Filed: Mar. 15, 1996

[86] PCT No.: PCT/JP96/00690

§ 371 Date: Jan. 7, 1997

§ 102(e) Date: Jan. 7, 1997

[87] PCT Pub. No.: WO96/29092

PCT Pub. Date: Sep. 26, 1996

[30] Foreign Application Priority Data

Mar. 17, 1995 [JP] Japan ........................ 7/58610

[51] Int. Cl.$^6$ ................... C07K 14/565; A61K 38/21

[52] U.S. Cl. .......................... 424/85.6; 530/351

[58] Field of Search ................ 530/351; 424/85.6

[56] References Cited

U.S. PATENT DOCUMENTS

| 4,548,900 | 10/1985 | Nobuhara et al. | 435/68 |
|---|---|---|---|
| 4,680,261 | 7/1987 | Nobukan et al. | 435/68 |
| 5,554,513 | 9/1996 | Revel et al. | 435/69.51 |

FOREIGN PATENT DOCUMENTS

| A 63-91331 | 4/1988 | Japan . |
|---|---|---|
| A 6-157344 | 6/1994 | Japan . |
| A 6-271478 | 9/1994 | Japan . |
| A 7-501320 | 2/1995 | Japan . |
| A 7-145071 | 6/1995 | Japan . |
| A 7-285882 | 10/1995 | Japan . |
| A 8-81389 | 3/1996 | Japan . |

*Primary Examiner*—Lila Feisee
*Assistant Examiner*—Geetha P. Bansal
*Attorney, Agent, or Firm*—Birch, Stewart, Kolasch & Birch, LLP

[57] ABSTRACT

The present invention relates to a corneal angiogenesis inhibitor which has interferon β as an active ingredient and which is used for preventing and treating neovascularization or invasion of vessels in the cornea.

3 Claims, 3 Drawing Sheets

INHIBITORY EFFECT OF INTERFERON ON VASCULAR ENDOTHELIAL CELL PROLIFERATION (in vitro)

EACH VALUE IS MEAN±SD (n=7)

*p<0.05 (vs control)
 **p<0.01 (vs control)
***p<0.001 (vs control)

INHIBITORY EFFECT OF INTERFERON ON VASCULAR ENDOTHELIAL CELL PROLIFERATION (in vitro)

EACH VALUE IS MEAN±SD

\*\*p<0.01 (vs control)
\*\*\*p<0.001 (vs control)

CORNEAL ANGIOGENESIS INHIBITOR

TECHNICAL FIELD

The present invention relates to a corneal angiogenesis inhibitor and also relates to a corneal angiogenesis inhibitor which is useful as a preventive or therapeutic agent to various kinds of diseases caused by abnormal vascular proliferation in the cornea.

BACKGROUND ART

Neovascularization is deeply involved in the onset and progress of various kinds of inflammatory diseases such as rheumatoid arthritis and psoriasis; ocular diseases such as diabetic retinopathy, retinopathy of prematurity, senile macular degeneration, retinal vein occlusion, retrolental fibroplasia, neovascularization associated with keratoplasty, glaucoma, and ocular tumors; and various kinds of tumors. In particular, it is known that neovascularization or invasion of vessels is observed in the corneas of patients with Stevens-Johnson syndrome and similar diseases; ocular pemphigoid and similar diseases; corneal chemical injuries caused by various kinds of agents having cytotoxicity, for example, alkaline, acid, detergents, various kinds of solvents, and volatile gases; trachoma; viral infections; phlyctenular keratitis; keratoplasty; and patients who use contact lenses for long periods. Aqueous chambers, lenses, and vitreous are originally transparent without vessels, and if neovascularization occurs in these tissues, severe visual loss occurs, resulting in difficulties in everyday life. Therefore, agents which inhibit neovascularization have recently been considered for development as preventive or therapeutic agents for the above-mentioned diseases.

Examples of such angiogenesis inhibitors reported up to the present are as follows: protamine application (Taylor, S. et al., Nature, 297, 307, 1982), a combination of heparin and cortisone (Folkman, J. et al., Science, 221, 71, 1983), prednisolpne-acetate (Robin, J. B., Arch. Opthalmol., 103, 284, 1985), sulfonated polysaccharide (Japanese Patent Laid-Open No. 63-119500), Herbimycin A (Japanese Patent Laid-Open No. 63-295509), Fumagillin (Japanese Patent Laid-Open No. 1-279828). However, these angiogenesis inhibitors are unsatisfactory as preventive or therapeutic agents because of insufficient activity and side effects, such as toxicity; thus, useful agents in inhibiting neovascularization have been expected. Particularly in the ocular field where it is necessary to use medicines while maintaining ongoing visual functions, the development of safe medicines which have no adverse effects on other ocular tissues has been awaited.

Concerning interferon α, the therapeutic possibly for ocular diseases accompanied with neovascularization is suggested in cases of age-related macular degeneration (Fung, W. E. Am. J. Ophthalmol., 112, 349 1991), neovascular glaucoma (Miller, J. W. et al. Ophthalmology, 100, 9 1992), and diabetic retinopathy (Wakelee-Lynch, J. and Banks, P., Diabetes Care, 15, 300, 1992), though the practical usefulness is still unknown.

An object of the present invention is to provide an useful corneal angiogenesis inhibitor.

DISCLOSURE OF THE INVENTION

The present invention is a corneal angiogenesis inhibitor having interferon β as an active ingredient.

BEST MODE FOR CARRYING OUT THE INVENTION

Figure 1:
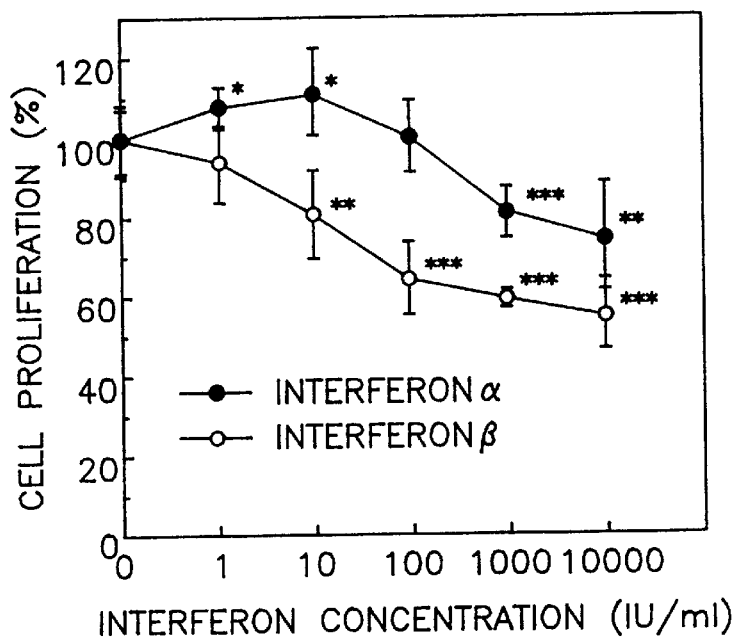
FIG. 1 shows the results of Example 1 of the present invention and FIG. 2 shows the results of Example 2 of the present invention.

The diseases which are the subjects of the present invention are those accompanied with neovascularization in the cornea, and the present invention is preferably used for patients with Stevens-Johnson syndrome and similar diseases thereof; ocular pemphigoid and similar diseases thereof; corneal chemical injuries caused by various kinds of agents having cytotoxicity, for example, alkaline, acid, surface active agents, various kinds of solvents, and volatile gases; trachoma; viral infections; phlyctenular keratitis; keratoplasty; and patients who use contact lenses for long periods.

A corneal angiogenesis inhibitor of the present invention is used as a preventive agent in addition to use as a therapeutic agent for neovascularization in the cornea.

Interferon used for the present invention may be a β type, a consensus type containing a β-type amino-acid sequence, or a hybrid type; and although any origin type of interferon can be used such as natural types, gene-recombinant types, and chemically synthesized types, interferon β of a natural or gene-recombinant type is preferably used among these. It has been suggested that interferon α is applicable to the treatment of ocular diseases accompanied with certain kinds of neovascularization, however, as a result of in-depth study, the inventors of the present invention have found that interferon β exhibits much more potent angiogenesis inhibition than interferon α, and completed the present invention.

Fibroblasts and an established cell line thereof are preferably used for producing a natural type interferon β. When interferon is prepared by a gene recombinant technique, the following materials are used as the host cells: CHO (chinese hamster ovarium) cells; mammal cells, such as mouse C127 cells; insect cells, such as silkworm and spodoptera frugiperda; and microorganisms, such as *Escherichia coli*, *Bacillus subtilis*, and yeast. Further, mouse, rat, hamster, rabbit, goat, sheep, swine, and bovine cells can be used.

Using various kinds of chromatographies, the thus-prepared interferon β can be purified and isolated from materials, such as supernatants of cell cultures, extracts of insects, extracts of bacteria, and extracts of organisms. Any chromatography may be used if it has an affinity for interferon β; for example, chromatography employing silicon dioxide (silica) as an absorbent, chromatography employing heparin, a dye, or a hydrophobic group as a ligand, metal-chelate chromatography, ion exchange chromatography, and gel filtration chromatography may be used.

Interferon β used in the present invention can be orally or parenterally administered as it is or as a pharmaceutical composition mixed with pharmacologically acceptable known carriers, excipients, and the like.

Practical dosage forms suitable for oral administration are tablets, pills, capsules, granules, syrups, emulsions, suspensions, and the like. These dosage forms are prepared according to known methods and they contain carriers or excipients generally used in the pharmaceutical field. Examples of these carriers and excipients for tablets are lactose, maltose, saccharose, starch, and magnesium stearate.

Examples of dosage forms for parenteral administration are eye drops, ointments, injections, stupes, liniments, suppositories, nasal preparations, aerosol inhalational preparations, transdermal preparations, and implantable slow-release preparations. Solution forms can be prepared according to known methods, for example, by dissolving interferon in a sterilized aqueous solution generally used for injections, by suspending interferon in an extract, or by embedding interferon in liposomes after emulsifying. Solid forms can be prepared as lyophilized materials according to known methods, for example, by adding mannitol, trehalose, sorbitol, lactose, glucose, or the like, as an excipient, to interferon β. Gel forms can be prepared according to known methods, for example, by dissolving interferon β in thickeners and polysaccharides such as polyethylene glycol, methyl cellulose, carboxymethyl cellulose, hyaluronic acid, and chondroitin sulfate; and the solid-form interferon β can be also used for the gel forms after being pulverized.

To any dosage form, human serum albumin, human immune globulin, α2 macroglobulin, amino acids, and the like may be added as stabilizers; and alcohols, sugaralcohols, ionic detergents, nonionic detergents, and the like may be added as dispersing agents or as absorbefacients, unless these impair the bioactivity of interferon β. Further, trace metals and organic salts may be added, if required.

More practically, the natural-type interferon β preferably used for the present invention is obtained from the following method.

In general, interferon β producing cells are cultured on the surface of glass, plastic, DEAE-dextran microcarriers, or the like, and then receive an induction treatment using synthetic double-stranded RNA such as Poly I:C, followed by a super-induction treatment (such as a metabolic inhibition method utilizing a combination of cycloheximide and actinomycin D, or a ultraviolet-radiation method). The cells are then cultured for 20 to 48 hr. in a medium in which interferon β is produced; the medium is then recovered as a liquid comprising human interferon β.

In general, since the concentration of interferon β obtained by the above-mentioned method is low, and the culture medium includes many impurities from cells and additives, it is necessary to concentrate and purify interferon β for medical use. Chromatography using insoluble carriers bonded to a blue dye and those carriers which are bonded to metal-chelate groups is preferably employed for concentration and purification of interferon β, though this method is not restrictive. In other words, a culture medium containing crude interferon β is arranged to be in contact with the insoluble carriers bonded to a blue dye, then the absorbed interferon β is recovered as a solution by an eluant. The interferon β solution is then allowed to be in contact with the carriers bonded to metal-chelate groups, for example, those obtained by chelating zinc, and recovered as concentrated and purified interferon β by an eluant.

It is particularly preferable to form the thus-obtained interferon β preparation into the above-mentioned dosage forms to use as a corneal angiogenesis inhibitor.

Although the treatment dose of interferon β used in the present invention is appropriately determined according to the age, weight, disease, and symptoms of the patient, the method and route of administration, and the like, the dose generally ranges from 10,000 to 10,000,000 unit/day and, preferably, 100,000 to 6,000,000 unit/day.

The present invention is described in more detail by reference to the following examples, though the present invention is not limited to these examples.

EXAMPLES

Example 1

Detection of anti-Proliferative effect on endothelial cells derived from human umbilical vein Vascular endothelial cells were inoculated on a 24-well plastic plate and cultured in an M199 medium containing 10% fetal calf serum. After 24 hours, the medium was removed, and then another medium containing 0 to 10,000 IU/ml of a natural type interferon α ("Sumiferon") or a natural type interferon β (Feron, manufactured by Toray Industries, Inc.) was added thereto. Three days after adding interferon, the number of cells were counted using a colter counter and the proliferation was expressed as a percentage of total proliferation occurring over the same period in control groups which had not received any interferon. As is shown in FIG. 1, interferon β inhibited the proliferation of the vascular endothelial cells in a concentration-dependent manner with a statistically significant difference. On the contrary, the natural type interferon α at low concentrations, i. e., 1 to 10 IU/ml, enhanced the proliferation of the vascular endothelial cells and, although, interferon α inhibited the proliferation at 1,000 IU/ml or more, the inhibitory effect on the vascular endothelial cells was apparently weaker than that occurring to cells treated with interferon β.

Example 2

Figure 2:
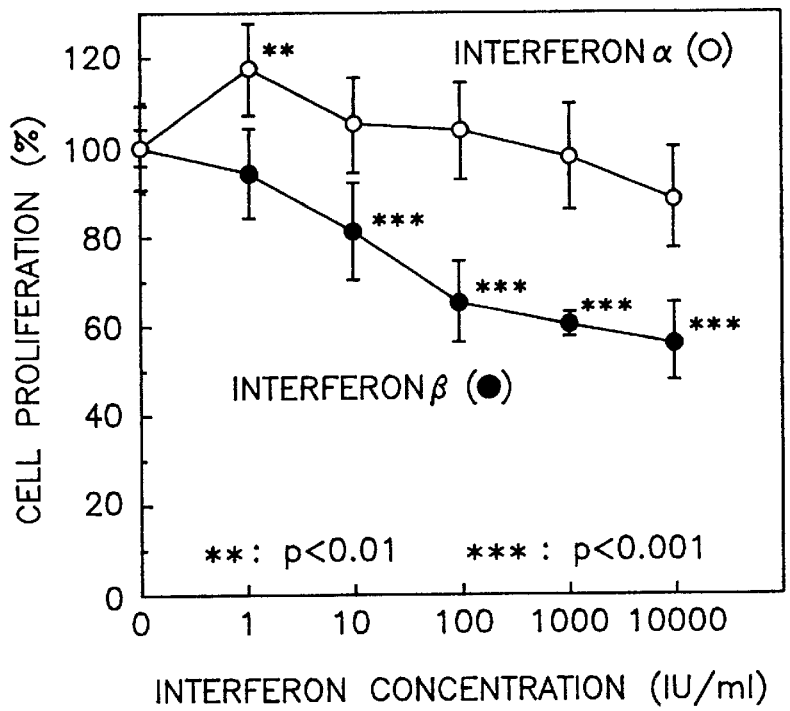

Detection of anti-proliferative effect on endothelial cells derived from human umbilical vein Vascular endothelial cells were inoculated on a 24-well plastic plate and cultured in an M199 medium containing 10% fetal calf serum. After 24 hours, the medium was removed, and then another medium containing 0 to 10,000 IU/ml of a recombinant type interferon α (Roferon, manufactured by Nippon Roche K.K.) or a natural type interferon β (Feron, manufactured by Toray Industries, Inc.) was added thereto. Three days after adding interferon, the number of cells were counted using a colter counter and the proliferation was expressed as a percentage of total proliferation occurring over the same periods in control groups which had not received any interferon. As is shown in FIG. 2, interferon β inhibited the proliferation of the vascular endothelial cells in a concentration-dependent manner with a statistically significant difference. On the contrary, the recombinant type interferon α at low concentrations, i.e., 1 to 100 IU/ml, enhanced the proliferation of the vascular endothelial cells and did not significantly inhibit the proliferation of the vascular endothelial cells.

Example 3

Detection of angiogenesis inhibitory effect of interferon β on vascular angiogenesis using a rabbit corneal micropocket method This example was carried out according to the method described Gimbrone et al. [J. Nat. Cancer Inst. 52:413–419 (1974)].

Ethylene/vinyl acetate copolymer (EVA) was dissolved in methylene chloride (8% solution) and dropped on a silicone plate, followed by drying. Basic fibroblast growth factor (bFGF) was dropped thereon followed by drying, and then an EVA solution was further applied thereon followed by drying. The resulting sheet having a sandwich-like structure was rolled and used as a pellet for transplantation.

Under anesthesia, two pellets were transplanted in each cornea of rabbits (NZW, male); and 0 to 9 MIU/kg of the natural type interferon p used in Example 1 was administered via auricular veins for ten consecutive days. Corneal examination was carried out on the 4th, 7th, and 10th days and the inhibitory effect was evaluated based on the incidence and calipered length of neovessels. As is shown in Table 1, interferon β showed strong inhibition against neovascularization in a dose-dependent manner.

TABLE 1

| Interferon | Angiogenesis Inhibition | | | | | |
|---|---|---|---|---|---|---|
| | Neovessel length (m) | | | Neovessel incidence | | |
| (MIU/kg) | day 4 | day 7 | day 10 | day 4 | day 7 | day 10 |
| 0 | 0.5 ± 0.1 | 1.7 ± 0.5 | 2.5 ± 1.0 | 8/8 | 8/8 | 8/8 |
| 0.3 | 0.4 ± 0.0 | 1.4 ± 1.0 | 1.8 ± 1.3 | 8/8 | 6/8 | 6/8 |
| 3.0 | 0.2 ± 0.2 | 1.0 ± 0.3 | 0.8 ± 1.2* | 3/8 | 8/8 | 3/8 |
| 9.0 | 0.2 ± 0.2 | 1.0 ± 0.5 | 0.8 ± 0.8* | 4/8 | 7/8 | 5/8 |

*: $p < 0.01$

Example 4

Detection of angiogenesis inhibitory effect of interferon β and interferon α against vascular angiogenesis using a rabbit-cornea micro-socket method This example was carried out according to the method described by Gimbrone et al. [J. Nat. Cancer Inst. 52:413–419 (1974)].

EVA was dissolved in methylene chloride (8% solution) and dropped on a silicone plate, followed by drying. bFGF was dropped thereon followed by drying, and then an EVA solution was further applied thereon followed by drying. The resulting sheet in a sandwich-like shape was rolled and used as a pellet for transplantation.

Figure 3:
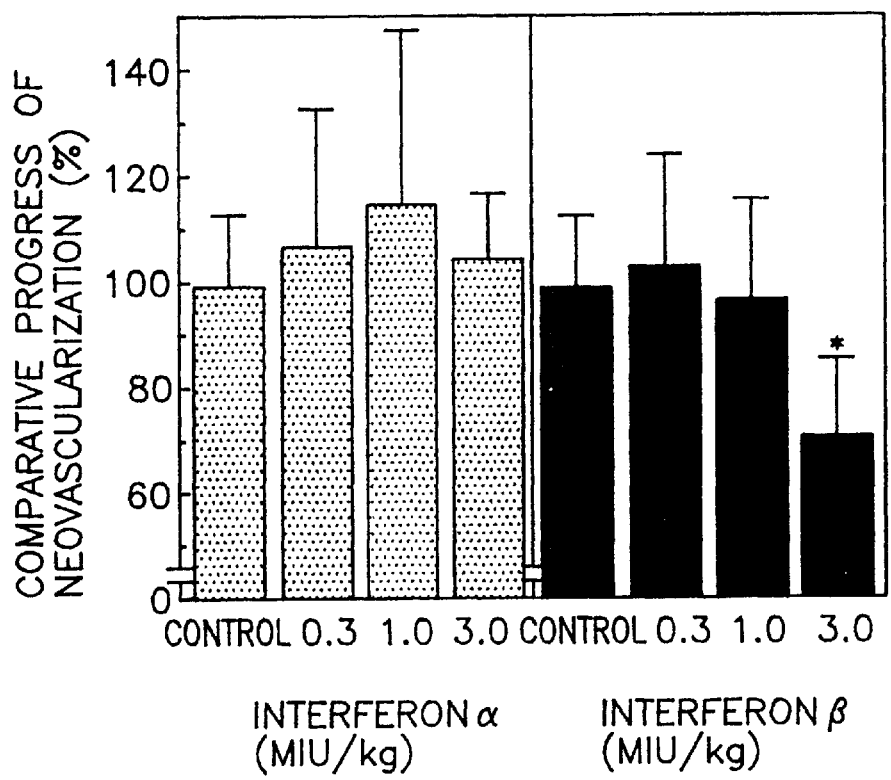
FIG. 3 shows the results of Example 4 of the present invention.

Under anesthesia, two pellets were transplanted in each cornea of rabbits (NZW, male); and 0 to 3 MIU/kg of the recombinant type interferon α or the natural type interferon β, both used in Example 2, was administered via auricular veins for seven consecutive days. Corneal examination was carried out on the 7th day and the inhibitory effect was evaluated based on the calipered length of neovessels. The results were expressed as percentages to control groups (0 MIU/kg). As is shown in FIG. 3, although the recombinant type interferon α did not significantly inhibit the neovascularization, interferon β showed strong inhibitory effect on neovascularization in a dose-dependent manner.

Industrial Applicability

A corneal angiogenesis inhibitor of the present invention, which contains interferon β as an active ingredient, is employed as a preventive and a therapeutic agent for neovascularization or invasion of vessels in the cornea caused by ocular diseases accompanied with neovessels.

What is claimed is:

1. A method for treating corneal neovasculariztion which comprises:

administering an effective amount of interferon β for treating corneal neovascularization by inhibiting the proliferation of vascular endothelial cells, to a patient with corneal neovascularization.

2. A method for inhibiting angiogenesis which comprises administering an effective amount of interferon β for treating corneal neovascularization by inhibiting the proliferation of vascular endothelial cells, to a patient in need thereof.

3. A method for treating corneal neovascularization according to claim 1, wherein said patient has a condition selected from the group consisting of Stevens-Johnson syndrome, ocular pemphigoid, corneal chemical injuries caused by cytotoxic agents, trachoma, viral infections, phlyctenular keratitis, keratoplasty, and injuries caused by wearing contact lenses for long periods of time.

* * * * *